United States Patent [19]

Stinson

[11] Patent Number: 5,047,348

[45] **Date of Patent: * Sep. 10, 1991**

[54] APPARATUS FOR HOUSING RADIOACTIVE ITEMS DURING INCUBATION

[75] Inventor: Margaret C. Stinson, N. Billerica, Mass.

[73] Assignee: Massachusetts Institute of Technology, Cambridge, Mass.

[ * ] Notice: The portion of the term of this patent subsequent to Dec. 25, 2007 has been disclaimed.

[21] Appl. No.: 413,163

[22] Filed: Sep. 27, 1989

Related U.S. Application Data

[63] Continuation-in-part of Ser. No. 335,836, Apr. 10, 1989.

[51] Int. Cl.[5] .......................... C12M 1/12; C12M 1/22

[52] U.S. Cl. .................................... 435/311; 435/298; 435/809; 55/385.1; 55/385.2; 55/385.4; 55/387; 55/478; 422/159

[58] Field of Search ................ 55/DIG. 9, 387, 385.1, 55/385.2, 385.4, 478; 435/34, 35, 807, 311, 313, 298, 809; 422/159

[56] References Cited

U.S. PATENT DOCUMENTS

| | | | |
|---|---|---|---|
| 3,084,492 | 4/1963 | Dorsak et al. | 55/265 |
| 3,925,046 | 12/1975 | Hickey et al. | 55/387 |
| 3,964,887 | 6/1976 | Hickey et al. | 55/267 |
| 3,969,496 | 7/1976 | Schrot | 435/35 |
| 3,997,404 | 12/1976 | Waters | 435/35 |
| 4,057,470 | 11/1977 | Schrot | 435/35 |
| 4,127,397 | 11/1987 | O'Nan, Jr. et al. | 55/479 |
| 4,135,896 | 1/1979 | Parish et al. | 55/270 |
| 4,467,308 | 8/1984 | Kleinhammer et al. | 435/7 |
| 4,592,192 | 6/1986 | Jacob et al. | 53/512 |
| 4,670,398 | 6/1987 | Song | 435/298 |
| 4,773,922 | 9/1988 | Ross et al. | 55/DIG. 9 |
| 4,935,371 | 6/1990 | Rickloff | 435/298 |

OTHER PUBLICATIONS

Neel et al, *Sequences*, Issue 33, Winter 1990, p. 5.

*Primary Examiner*—Brooks H. Hunt
*Assistant Examiner*—Ngoclan T. Mai
*Attorney, Agent, or Firm*—Thomas J. Engellenner; William C. Geary, III

[57] ABSTRACT

An apparatus for housing radiation-emitting items to be incubated, such as radio-labeled cell cultures, in order to prevent contamination of the interior of an incubator and the surrounding environment. The apparatus is nonporous and preferably relatively thermally resistant. Additionally, the apparatus features a selectively sealable lid and has at least one opening within which is disposed a filter for entrapping any radioactive compounds contained in gases exiting the apparatus during incubation. The apparatus is used in conjunction with known incubation procedures of radiolabelled cell cultures or other items.

6 Claims, 2 Drawing Sheets

APPARATUS FOR HOUSING RADIOACTIVE ITEMS DURING INCUBATION

CROSS-REFERENCE TO RELATED APPLICATION

This is a continuation-in-part application of U.S. Ser. No. 335,836 filed on Apr. 10, 1989.

BACKGROUND OF THE INVENTION

The present invention relates to a method and apparatus for incubating radioactive items such as cell cultures and the like.

In the course of biological and medical research, radioactive isotopes are added to cell cultures which subsequently are incubated. For example, $^{35}S$ amino acids, such as cysteine and methionine, can be added to cell culture media. The cells and the culture media are then incubated at 37° C. under conditions which do not inhibit oxygen and carbon dioxide exchange. During incubation volatile radio-labelled compounds, such as $CH_3{}^{35}SH$, are produced and can escape into the environment of the incubator, contaminating interior walls, shelves, trays, fans and other components. Such procedures obviously pose serious health risks to researchers and others who come into contact with the incubators, their contents and the surrounding environment.

Attempts have been made to alleviate or minimize the radiation contamination of incubators. These include placing trays of activated charcoal within the incubator, or placing charcoal sticks or Packets within the incubator. Although helpful to some extent, such techniques tend only to reduce the risk of radiation contamination and do not entirely eliminate the problem.

There is thus a need for safe, effective techniques and equipment for preventing the radiation contamination of the interior of incubators. Current practices for dealing with radioactive emissions from incubating cells or other items are not entirely effective.

It is therefore an object of the present invention to provide methods and devices for capturing and retaining emissions of radioactive gases from radio-labelled incubating cells. A further object of the invention is to provide a method and apparatus to facilitate safe incubation of radio-labelled cells or other items in such a way that volatile radioactive compounds are not released into the incubator or the surrounding environment. Additional objects will be apparent to those of ordinary skill in the art upon reading the following disclosure.

SUMMARY OF THE INVENTION

Methods and systems are disclosed which enable radio-labelled cells or other items to be incubated in such a way that radioactive gases do not escape into the environment during the incubation procedure.

In one embodiment, the apparatus consists of a specially adapted container, with a filter apparatus, for housing the radio-labelled cells or other items during the incubation procedure. Preferably, this radiation filtration container is constructed of a material which is nonporous and impervious to at least low energy beta emitters or at least to removable radioactive contamination. Additionally, the container has at least one opening into which a filter may be inserted. The filter functions to entrap radioactive compounds which may be contained within gases exiting the container during the incubation procedure. The filter is disposed within the opening of the container such that gas may exit the container only by passage through the filter.

Filter elements useful in the present invention can be of virtually any size, shape and construction sufficient to entrap any radioactive material contained in a gas exiting the container. Preferably, the filter has a flow path within which is disposed an absorbent material such as activated charcoal. Further, filtration and entrapment of larger particulates may result when glass wool or similar materials are used in conjunction with the activated charcoal.

DETAILED DESCRIPTION OF THE DRAWINGS

The present invention provides a radiation filtration container 10 which enables radio-labelled cells or other items to be incubated without a release into the interior of the incubator of volatile radioactive materials.

Figure 1:
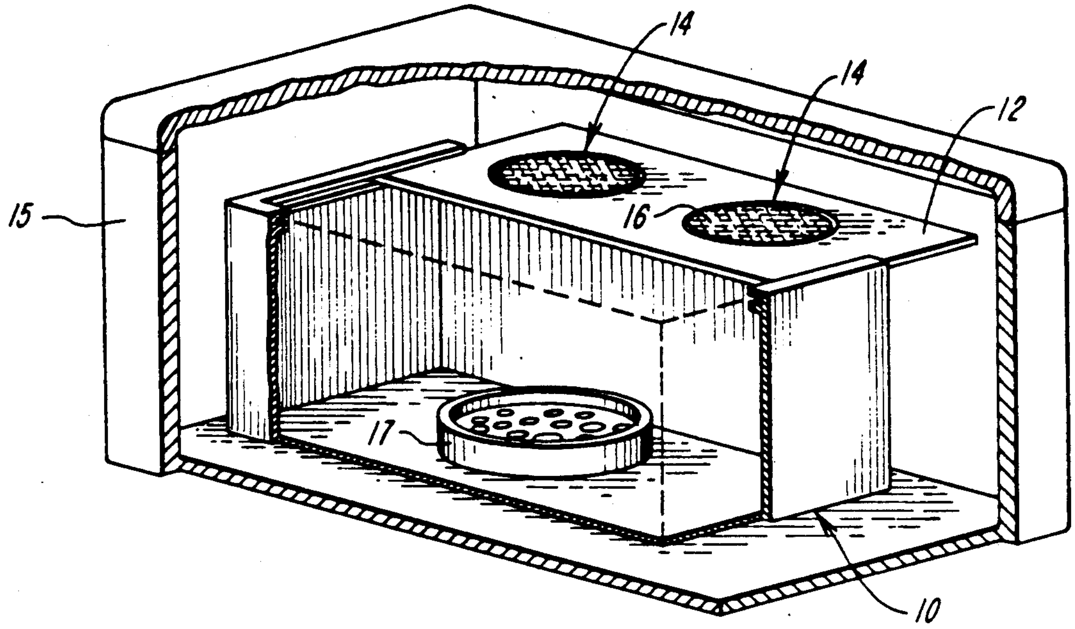
FIG. 1 is a perspective view of a radiation filtration container of this invention, disposed within an incubator.
Figure 2:
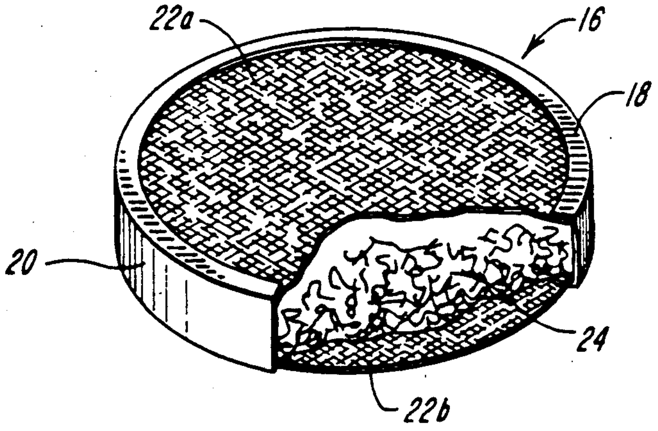
FIG. 2 is a perspective view, Partially cut away, of a filter cartridge useful with the radiation filtration container of FIG. 1.
Figure 3:
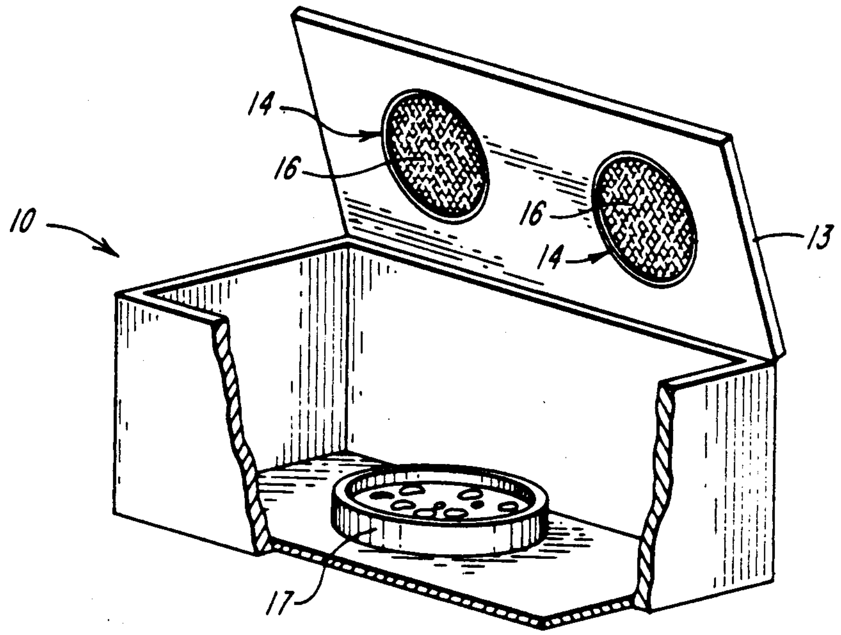
FIG. 3 is a perspective view of another embodiment of a radiation filtration container according to the present invention.

Referring to FIGS. 1 and 2, the apparatus 10 of the present invention may feature a rigid or substantially rigid container preferably constructed of a nonporous polymeric material. FIG. 1 illustrates one embodiment of the invention comprising a rigid container apparatus 10 having a removable lid 12 and one or more vent holes 14 disposed in the top surface of the lid. Seated within the vent holes are filter elements 16 which are removably and replaceably secured within the vent holes. Container 10, as illustrated in FIG. 1, is disposed within an incubator 15, and houses a cell culture 17.

Where the apparatus 10 of the present invention consists of a rigid or substantially rigid container, as shown in FIGS. 1 and 3, it may be constructed of a nonporous, rigid polymer such as acrylic, styrene acrylonitrile based polymers, as well as low density polyethylene or other suitable polymers or copolymers which effectively shield or contain low energy beta emitters or removable radioactive contamination, especially $\beta^{31}$ ray radiation. In some embodiments, it may be preferable to utilize transparent or translucent polymers, however, opaque polymers may also be used. Exemplary products include the acrylic beta radiation shields sold by a number of manufacturers, including Research Products International Corp. of Mount Prospect, Ill. and the radiation boxes available from Owl Scientific Plastics of Cambridge, Mass. Also, Nalgene utility boxes, manufactured by the Nalge Company and constructed of a styrene-acrylonitrile copolymer box and a friction fit, low density polyethylene lid may be used as well. The rigid container 10 may be of virtually any shape, however square or rectangular containers often are preferred. Also, the size of the container may vary depending upon the applications with which it is to be used. Typically, a rectangular rigid container has a preferred size of approximately 12×24×6 inches so as to be useful in conventional incubators.

As shown in FIGS. 1 and 3, rigid container 10 preferably features a lid 12, 13 which may be either removable and replaceable (e.g., as in FIG. 1), or openable by way of hinge (e.g., as in FIG. 3). In any event, the container 10 is designed using a lid means such that when the lid 12, 13 is in the closed position it may be securely sealed to prevent any exit of gas through the seam of the lid. In one embodiment the lid 12 may be slideably joined to and seated upon the main portion of the container 11 as in FIG. 1. Alternatively, as shown in FIG. 3, the lid may have a natural (i.e., polymeric) hinge or a mechanical hinge and a locking element (not shown) which ensures that the lid 13 may be maintained in a closed position. In another embodiment (not shown) the lid may be mounted upon its associated container using a frictional fit. If desired, the lid or container can further include a rim-sealing gasket or the like.

The filter element 16 used in conjunction with rigid container 10 is preferably a cylindrical cartridge containing activated charcoal in Particulate or granular form. FIG. 2 illustrates one embodiment of a filter cartridge 16 useful with the present invention. As shown in FIG. 2, the filter has a housing 18 constructed of a material such as a metal or plastic. The housing 18 has a side wall and top and bottom surfaces. The side walls 20 of the housing are preferably solid while the top and bottom surfaces *22a*, *22b* of the housing are mesh-like, featuring a number of very small holes to allow the passage of gas therethrough. Preferably, the mesh size of the top and bottom surfaces *22a*, *22b* is between about 1/32 and 1/16 of an inch. In the illustrated embodiment, an absorbent material 24 such as activated charcoal, in particulate or granulated form, is disposed within the interior of filter 16. Exemplary filters useful in the present invention are available from Mine Safety Appliances of Esmond, R.I. Similarly useful filters are manufactured of activated charcoal set in a paper matrix and are available from Schleicher & Schueller Inc. of Keene, N.H.

The filters may be of virtually any size and shape provided they fit securely within opening 14 in lid 12, 13. Preferably, however, the filters are of a circular shape and of a size sufficient to fit securely within an opening 14 of about 2.2 inches in diameter. In an alternative embodiment (not shown), the filter(s) may be larger than the opening in the lid and are securely disposed, overlapping the opening. Although FIGS. 1 and 3 illustrate the use of two filters, it is understood that one of ordinary skill in the art may deem it suitable to use virtually any number of filters.

The filter 16 is operably disposed within the vent holes 14 of the rigid container 10 so that gases exit the container through the filter or filters. While exiting the container through filter 16, any radioactive compounds entrained within existing gases will be trapped within the absorbent filter material 24 of the filters. Accordingly, the gases exiting the container 10 and passing into the environment of the autoclave will be free of radioactivity.

Typically, cell cultures which are to be incubated contain viable cells which require oxygen in order to maintain metabolic activity. Thus, although the container apparatus itself is substantially airtight, air is able to pass into and out of the container 10 through filters 16. In this way, cell viability is maintained and gases exiting the containers are filtered to remove any entrained radioactive compounds.

The present invention can be utilized by selecting the appropriate container for housing the cells or other items to be incubated. The materials to be incubated, such as radio-labelled cell cultures, can then be disposed within the interior of the container. The filter is then securely sealed within the opening or openings of the container, and the container is placed within an incubator which is then activated. The conditions under which incubation take place may vary depending upon the requirements of a given application. These conditions may be determined by one having ordinary skill in the art.

Following the incubation procedure, the interior walls and components of the incubator should be free of radation as the emitted radiation will have been absorbed by the filter(s). The container and filter(s) may then be handled and disposed of in a manner conventional for radioactive solid waste materials.

Although the present invention has been described with respect to currently preferred embodiments, those having ordinary skill in the art may make modifications and variations to the invention without exceeding the scope of the invention. For example, the design of filters and the filtering material useful with the embodiments of the invention may be altered. Various filter materials can be used in lieu of carbon or charcoal, including ceramics having absorbent materials incorporated into the porous channels of a ceramic matrix, or fibrous matrices, again incorporating absorbent materials. Additionally, the gases passing through the filter need not be vented into the incubator environment but rather they can be trapped in another portion of the containment means or in an auxilliary container for disposal. Also, changes may be made to the method of seating the filter or filters within the waste container, again without exceeding the scope of the present invention.

The following example serves to further describe the invention.

EXAMPLE

Radiation measurements, using a liquid scintillation counting detector, were taken of the interior of a clean incubator and a clean radiation filtration container of the type described above before use. In each instance the radiation count was below minimum detectable activity.

A culture of cells to be incubated was labelled with 0.8 microcuries $^{35}$S cysteine and 0.8 microcuries 35S methinine was placed within a multiwell tissue culture plate which, in turn, was placed within a radiation filtration container of the type described above having activated charcoal-containing filter cartridges. The culture was incubated for approximately 3 hours at 55° C. Following incubation radiation readings were again taken of the interior walls of the incubator by rubbing an incubator wipe against the walls and measuring the level of radiation on the wipe using a liquid scintillation counting process. The level of radiation on the interior walls of the incubator was below minimum detectable level following the incubation process. The radiation level within the radiation filtration container was approximately 2502 DPM/100cm$^2$ following incubation.

What is claimed is:

1. An apparatus for housing radio-labelled items during incubation thereof, comprising:

a substantially square or rectangular container for housing cultures of radio-labelled cells disposed in cell culture containers, said container having a lid which selectively seals an opening in the container, said openings having an area substantially equal to that of a side of the container opposite the opening;

at least one filter-retaining vent opening disposed in the container means;

a filter cartridge means for securely fitting within the vent opening of the container such that gas exiting the container passes through the filter cartridge means and for entrapping radioactive compounds contained in gases exiting said container; and an activated charcoal, radiation-absorbing filter material housed within the filter cartridge means.

2. The apparatus of claim 1, wherein the container means comprises a rigid structure made of a nonporous, material sufficient to contain low energy beta emitters and removable radioactive contamination.

3. The apparatus of claim 2, wherein the container means is constructed of an acrylic material.

4. The apparatus of claim 2, wherein the container means is constructed of a styrene-acrylonitrile copolymer material.

5. The apparatus of claim 1 wherein the filter cartridge means is disposed within a vent opening in the lid of the container means.

6. An apparatus for housing radio-labelled items during incubation thereof, comprising:

a substantially square or rectangular container for housing cultures of radio-labelled cells disposed in cell culture containers, said container having a lid which selectively seals an opening in the container, said opening having an area substantially equal to that of a side of the container opposite the opening;

at least one filter-retaining vent opening disposed in the container; and a filter cartridge means for securely fitting within the vent opening of the container such that gas exiting the container passes through the filter cartridge means for entrapping radioactive compounds contained in gases exiting the container, the filter cartridge means comprising a structure corresponding in shape to the vent opening and having solid side walls and perforated top and bottom walls; and an activated charcoal radiation-absorbing filter material housed within said filter cartridge means.

* * * * *